United States Patent
Meier

(10) Patent No.: US 6,522,924 B1
(45) Date of Patent: Feb. 18, 2003

(54) PACEMAKER CAPABLE OF SENSING IMPEDANCE CHANGES IN MYOCARDIAL TISSUE

(75) Inventor: Jan Meier, Uttenreuth (DE)

(73) Assignee: Biotronik Mess-und Therapiegeraete GmbH & Co. Ingenieurbuero Berlin, Berlin (DE)

(*) Notice: Subject to any disclaimer, the term of this patent is extended or adjusted under 35 U.S.C. 154(b) by 0 days.

(21) Appl. No.: 09/599,593

(22) Filed: Jun. 22, 2000

(30) Foreign Application Priority Data

Jun. 23, 1999 (DE) .......................................... 199 29 553

(51) Int. Cl.$^7$ ............................................... A61N 1/365
(52) U.S. Cl. ............................................. 607/28; 607/6
(58) Field of Search ................................ 607/7, 11, 28, 607/19, 62; 600/547

(56) References Cited

U.S. PATENT DOCUMENTS

| | | |
|---|---|---|
| 4,303,075 A | 12/1981 | Heilman et al. |
| 4,527,568 A | 7/1985 | Rickards |
| 4,539,991 A | 9/1985 | Boute et al. |
| 4,554,921 A | 11/1985 | Boute et al. |
| 4,667,807 A | 5/1987 | Sanno |
| 4,686,987 A | 8/1987 | Salo et al. |
| 4,920,965 A | 5/1990 | Funke et al. |
| 4,951,667 A | 8/1990 | Markowitz et al. |
| 4,956,524 A | 9/1990 | Baker |
| 5,246,008 A | 9/1993 | Muellor |
| 5,282,840 A * | 2/1994 | Hudrlik ..................... 600/547 |
| 5,330,511 A | 7/1994 | Boute |
| 5,514,162 A * | 5/1996 | Bornzin et al. ............... 607/19 |
| 5,571,158 A * | 11/1996 | Bolz et al. ................... 607/121 |
| 5,713,933 A | 2/1998 | Condie et al. ................ 607/28 |
| 5,735,883 A | 4/1998 | Paul et al. |
| 5,766,230 A | 6/1998 | Routh et al. ................. 607/27 |
| 5,766,280 A | 6/1998 | Routh et al. |
| 5,792,197 A | 8/1998 | Nappholz .................... 607/17 |
| 5,824,019 A | 10/1998 | Rueter et al. ................ 607/17 |
| 5,843,137 A | 12/1998 | Condie et al. ................ 607/28 |
| 5,871,512 A | 2/1999 | Hemming et al. ............ 607/28 |

FOREIGN PATENT DOCUMENTS

| | | |
|---|---|---|
| DE | 195 07 929 A1 | 9/1996 |
| DE | 195 07 929 | 9/1996 |
| EP | 0 399 063 | 11/1990 |
| EP | 0 495 293 A1 | 7/1992 |
| EP | 0 765 671 | 4/1997 |
| WO | WO/98/19739 | 5/1998 |

OTHER PUBLICATIONS

B. H. Bostock, The Strength–Duration Relationship for Excitation of Myelinated Nerve: Computed Dependence on Membrane Parameters; J. Physiol. (1983) 341, pp. 59–74.

C. S. Herniquez et al., "Simulation of Propagation Along a Cylindrical Bundle of Cardiac Tissue—II: Results of Simulation", IEEF: Transactions on Biomedical Engineering, vol. 37, No. 9, Sep. 1990, pp. 861–875.

(List continued on next page.)

Primary Examiner—Kennedy Schaetzle
Assistant Examiner—Kristen Droesch
(74) Attorney, Agent, or Firm—Christie, Parker & Hale, LLP

(57) ABSTRACT

A capture-detection cardiac pacemaker wherein a stimulation success can be reliably detected immediately after stimulation pulse output. The cardiac pacemaker according to this invention generally includes at least one stimulation electrode arranged in the region of the heart designed to output stimulation pulses to the heart, and a control unit connected to a pulse generator for controlling the stimulation pulse output. The control unit is connected to a sensor arranged at the myocardium for checking stimulation success at the heart by detecting the myocardial impedance pattern immediately after a stimulation pulse output and still within the diastolic phase of the heart, and controlling the stimulation pulse output based thereon.

34 Claims, 2 Drawing Sheets

OTHER PUBLICATIONS

E. Gersing, "Impedanzspektroskopie als Hilfe bei Herzoperationen", Medizinelektronik, 9, 1982; pp. 88–89.

M. Osypka et al., Tissue Impedance Spectra and the Appropriate Frequencies for EIT, Physiol. Meas. 16 (1995) pp. A49–A–55.

A. M. Pichlmaier, Intrakardiale Impedanzmessung zur Bestimmung der Sympathikusaktivitat bei Frequenzadaptiver Electrostimulation—Teil 2: Klinische Ergbnisse, Biomedizinische Technik, Band 37, Heft 9/1992, pp. 188–193.

David, H. (Hrsg.): "Worterbuch der Medizin", Verlag Volk und Gesundheit, Berlin X002204248.

European Search Report for related European Application, EP 00 25 0195; dated Jul. 4, 2002.

* cited by examiner

PACEMAKER CAPABLE OF SENSING IMPEDANCE CHANGES IN MYOCARDIAL TISSUE

FIELD OF THE INVENTION

A capture-detection cardiac pacemaker, and particularly a capture-detection cardiac pacemaker adapted to stimulate the heart based on variations in impedance in the myocardial impedance pattern.

BACKGROUND OF THE INVENTION

This invention is generally directed to capture-detection cardiac pacemakers. Capture-detection cardiac pacemakers of the kind described herein are generally equipped with impedance measuring sensor means for checking the success of a pacemaker to induce stimulation of the heart. As is known, cardial impedance variations make it possible to determine the state of various cardiac functions, and in particular stimulation success. Accordingly, by monitoring stimulation success, it is possible to automatically adapt the stimulation pulses generated by the cardiac pacemaker to the stimulation stimulus threshold. Specifically, the stimulation stimulus threshold identifies the stimulation amplitude required to generate a stimulation success, i.e., a stimulated systole. As this stimulation stimulus threshold changes constantly as a consequence of hormone level, time of day, physical activity and so forth, the stimulation amplitude should be adapted to the variation of the stimulation stimulus threshold. If, for example, a sub-threshold stimulation is detected by virtue of an absence of stimulation success after the output of a stimulation pulse (as measured by the absence of a rise in impedance in the impedance pattern after output of the stimulation pulse), the stimulation amplitude should be increased. Such a dynamic variation of the stimulation amplitude ensures reliable operation of the cardiac pacemaker.

On the other hand, during the operation of the cardiac pacemaker the minimum energy required to provide stimulation should be used to guarantee a long service life for the battery, which is typically integrated in the cardiac pacemaker. Therefore, the stimulation amplitude should be increased only as far as necessary, i.e., only slightly above the stimulation stimulus threshold.

Besides checking the stimulation success on the basis of impedance measurement, methods are also generally known which measure the potential evoked by the stimulation pulse, or the QRS-complex. In this case, however, reliable detection of the stimulation success is only possible, at the earliest, between 100 and 130 milliseconds after output of the stimulation pulse by the cardiac pacemaker. Accordingly, there is a very severe time delay, and this causes difficulties in providing short-term corrective measures via stimulation pulse control.

In contrast, U.S. Pat. No. 5,766,230 discloses a cardiac pacemaker in which the stimulation success is checked while the stimulation pulse is still being outputted. In this pacemaker, at the end of the otherwise rectangular stimulation pulse, the stimulation amplitude falls away sharply due to a suddenly higher current flow signaling the stimulation success, and that produces a falling curve in the pulse shape. That falling curve in the pulse shape is used to detect the stimulation success. Although such a system provides very quick measurement, there is the disadvantage that the occurrence of a stimulation success can only be detected if the pulse shape changes before the end of the stimulation pulse. Otherwise, it is not possible with this prior art device to detect a stimulation success. As simulation procedures have shown, stimulation amplitudes near the stimulation stimulus threshold only result in a stimulation success after a delay of up to 3 milliseconds. However, the stimulation pulse is already completed at the end of this delay time and would, accordingly, not be detected by the prior art system. Stimulation success consequently can be reliably detected with such a system only if the stimulation pulse amplitudes are markedly above the stimulation stimulus threshold, because under such conditions the stimulation success delay occurs during the pulse output. Accordingly, detection of a stimulation success is not reliably implemented with this method at stimulation pulse amplitudes near the stimulation threshold. On the other hand, if stimulation pulses of over-high amplitude are always produced to ensure more reliable detectability, an excessively high energy output is required.

In another example of a prior art system, U.S. Pat. No. 5,843,137 discloses a cardiac pacemaker which makes use of an intracardial impedance measurement for checking stimulation success. The cardiac pacemaker essentially comprises a pulse generator for generating stimulation pulses, which, under the control of a control unit, are outputted by way of an electrode, and sensor means for measuring physiological parameters which are related to the cardiac function and with which stimulation success can be evaluated by way of the control unit. The sensor means sense the changes in impedance and other physiological values which are related to a stimulated systole. The control unit is capable of distinguishing between a natural and a stimulated systole. In that way, the control unit can inter alia implement adaptive adjustment of the stimulation amplitudes, in relation to the stimulation stimulus threshold, in dependence on the stimulation success. In such a system, measurement of the cardial impedance is effected intracardially. For that purpose the impedance between two electrodes associated with the cardiac pacemaker is measured (page 12, lines 7 through 9). In this prior art system the electrodes are the housing of the cardiac pacemaker itself, electrode lines introduced in the ventricle or atrium, and ring electrodes. Measurement is usually effected in a cyclic procedure, that is to say at equidistant time intervals, the one electrode is supplied with a measurement voltage and the current which flows between the two electrodes is measured. Impedance is determined in a known manner as the quotient between the measurement voltage and the current.

While a cardiac pacemaker of the kind described in the '137 patent is capable of detecting stimulation success; there is the disadvantage that detection is only possible after the expiry of a relatively long period of time after the output of the stimulation pulse. This delay is caused by the requirement of an intracardial impedance measurement. The long period of time for measurement still prevents the adoption in good time of a corrective measure—such as a safety stimulation pulse—if stimulation success fails to appear. If, nonetheless, a safety stimulation pulse is outputted, the unnecessary stimulation pulse can disturb the cardiac cycle, i.e., the succession in respect of time of the diastolic and systolic phases of the heart.

SUMMARY OF THE INVENTION

The present invention is directed to a capture-detection cardiac pacemaker wherein a stimulation success can be reliably detected immediately after stimulation pulse output.

The cardiac pacemaker according to this invention generally comprises at least one stimulation electrode arranged in the region of the heart designed to output stimulation pulses to the heart, and a control unit connected to a pulse generator for controlling the stimulation pulse output. The control unit is connected to a sensor arranged at the myocardium for checking stimulation success at the heart by detecting the myocardial impedance pattern immediately after a stimulation pulse output and still within the diastolic phase of the heart, and controlling the stimulation pulse output based thereon. The appendant claims set forth advantageous developments of the invention.

The present invention includes the technical teaching that, for reliable detection of a stimulation success immediately after a stimulation pulse output, the sensor means should be arranged at the myocardium, and thus detect the myocardial impedance pattern directly after stimulation pulse output and still within the diastolic phase of the heart. The invention is also directed to a cardiac pacemaker in which the control unit controls the stimulation pulse output of the pulse generator based on the variations in impedance of the myocardial impedance pattern.

The invention relies on the fact that stimulation success is reflected in the pattern of myocardial impedance, more specifically during or in immediate succession to the stimulation pulse output by the cardiac pacemaker (approximately within between 2 and 10 milliseconds); and more precisely, in a phase in which the heart has not yet mechanically reacted to the stimulation pulse. The mechanical reaction time of the heart is between about 50 and 70 milliseconds. In contrast thereto, stimulation success based on the measurement of intracardial impedance is possible only at a markedly later time. The phenomenon of short-term detectability on the basis of myocardial impedance is based on electro-physiological events in the myocardium. The variations in the impedance pattern are caused predominantly by changes in the membrane properties and ion shifts between extracellular space and the interior of the cardiac muscle cell. In the event of a stimulation pulse output, the tissue impedance decreases greatly for a duration of between 1 and 2 milliseconds, due to the opening of the $Na^+$-channels and the subsequent rise in conductivity of the cell membranes that this entails. The impedance fall occurs approximately by a factor of 3. This event, which can be clearly detected by way of the sensor means, identifies the occurrence of a stimulation success, that is to say the systole of the heart. Utilizing this method, it is possible for the occurrence or the failure of stimulation success to be reliably detected immediately after stimulation pulse output.

A particular advantage of ultra-fast detection of stimulation success is that, besides conventional adaptive adjustment of the stimulation amplitudes to the stimulation stimulus threshold in dependence on the stimulation success, it is also possible to provide for the generation of a safety stimulation pulse in the event of a stimulation failure. The safety stimulation pulse can thus be outputted without the patient noticing, and does not disturb the cardiac cycle. Accordingly, using the system according to the present invention, adaptive adjustment of stimulation amplitudes is possible without the person wearing the cardiac pacemaker suffering from "skipped beats" as in the case of previously known methods for checking stimulation success. Furthermore, an otherwise necessary threshold test by the doctor can be eliminated.

In one embodiment, the safety stimulation pulse is preferably triggered by the control unit of the cardiac pacemaker in the event of a stimulation success of the heart failing to occur as a result of a sub-threshold stimulation. Alternatively, separate electronic means can be provided for that purpose.

In one embodiment, preferably the sensor means are integrated in the stimulation electrode. In such a system the sensor means and stimulation electrodes are disposed in an operatively integrated fashion. For example, the stimulation electrode can be formed in the manner of a fractal electrode. By means of a fractal electrode, it is possible to detect changes in the myocardial impedance pattern a few milliseconds after a stimulation pulse output. Only up to 2 milliseconds are required as a blanking time. In another set of embodiments, sensor means and stimulation electrodes of various configurations can be connected to the cardiac pacemaker.

In one embodiment, measurement of the myocardial impedance is effected on the basis of the current-voltage method. For that purpose, the sensor means are an electrode set preferably comprising at least two contacts which are arranged in spaced relationship on the myocardium. In such an embodiment, one contact is supplied with an alternating current by the pulse generator and the other contact, which serves as a measurement electrode, is connected to the control unit for ascertaining the myocardial impedance. To exclude any disturbing influence which may result from electrode polarization, which occurs beneath about 1 kilohertz, further mutually juxtaposed electrode sets can also be adopted.

In another embodiment of the invention, the measurement of the myocardial impedance is effected immediately prior to the stimulation pulse output in order to ascertain a variation in impedance in the myocardial impedance pattern. This pre-stimulation affords defined detection time windows which permit a comparison of variations in impedance at a minimum level of energy requirement. As a result, the energy requirement is low despite the measurement current, which is required by virtue of using the current-voltage method for measuring the myocardial impedance.

In accordance with a further embodiment of the invention, a system is provided to establish the extent by which the stimulation stimulus threshold is exceeded by ascertaining the time delay between the preceding supra-threshold stimulation pulse. Using such a system, the adaptive adjustment function of the stimulation pulses can be optimized in relation to the stimulation stimulus threshold.

In another embodiment of the invention, besides checking the stimulation success at the heart, the control unit also implements a check of natural heart actions. For the detection of natural heart actions, the control unit may continuously monitor the myocardial impedance pattern and ascertain a natural heart action by reference to a temporary fall in impedance in the myocardial impedance pattern without previous stimulation pulse output. This method is advantageously insensitive to, for example, myopotentials. In such an embodiment, in order to ensure reliable continuous monitoring of heart actions with a moderate energy requirement, the myocardial impedance pattern can be detected with a sampling rate of preferably about 500 Hz. This monitoring can be implemented over the entire period of time or—for further saving energy—in previously defined time windows.

BRIEF DESCRIPTION OF THE DRAWINGS

Further features of the invention are described hereinafter with reference to the accompanying drawings in which.

DETAILED DESCRIPTION OF THE PREFERRED EMBODIMENTS

Figure 1:
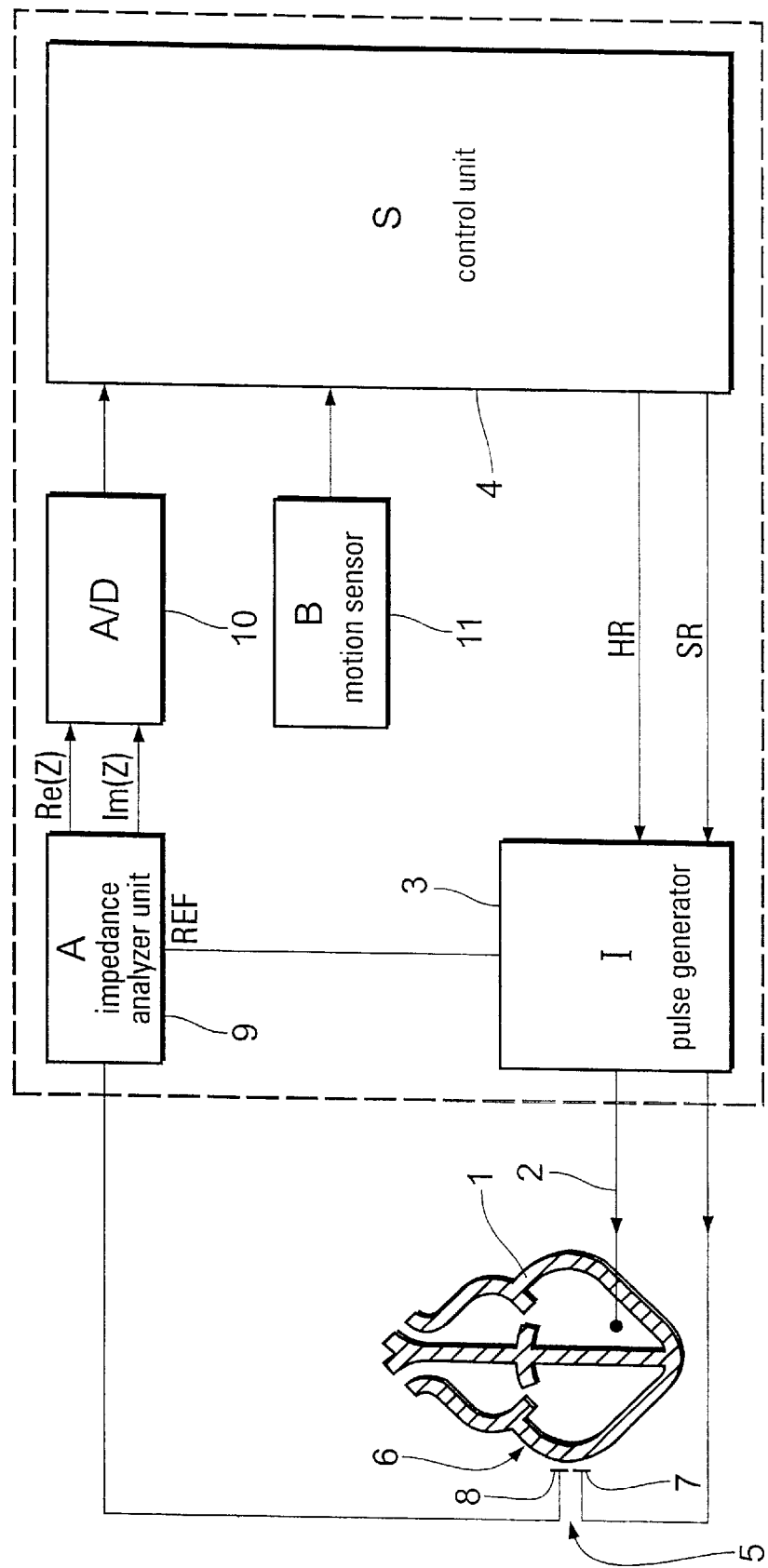
FIG. 1 is a block circuit diagram showing the principle of a cardiac pacemaker.

This invention is generally directed to capture-detection cardiac pacemakers. The cardiac pacemaker according to the invention, as shown in FIG. 1, is in the form of an activity-controlled cardiac pacemaker and can thus detect load-dependent activity parameters of its wearer—such as movement or heart rate in relation to daily cycle—and adjust the adaptive heart rate in dependence thereon.

For that purpose, disposed in the right ventricle of the heart 1 is a stimulation electrode 2. The stimulation electrode 2 serves to output stimulation pulses under the control of a pulse generator 3. Control of the pulse generator 3 is effected by way of a control unit 4, which outputs control signals corresponding to the heart rate (HR) ascertained thereby. FIG. 1 also shows sensor means 5 for detecting the impedance of the myocardium 6, being provided separately in order to better show the operating principle involved (preferably, however, the sensor means 5 are directly integrated in the stimulation electrode 2).

The value of the measured myocardial impedance is used in the control unit 4 for influencing the heart rate through the output of the stimulation pulses. The sensor means 5 include—in the illustrated embodiment—two contacts 7 and 8, which are gold-plated at their surfaces and which are fitted on the myocardium 6 at a suitable location. Preferably the contacts 7 and 8 are of a fractal geometry. The first contact 7 is connected to the pulse generator 3, which outputs measurement pulses in a controlled fashion at a sampling rate (SR) determined by the control unit 4. To save energy, the measurement pulses at the sampling rate (SR) are only outputted during defined time windows. Alternatively, the measurement pulses can also be outputted by way of the stimulation electrode 2. The contact 7 may then be eliminated or used as a redundant.

The measurement current used in the measurement pulses is about 10 microamps (effective), which penetrates several millimeters deep into the myocardium 6 and is kept constant by the control unit 4 in order to minimize the measurement error. The second contact 8, which serves as a measurement electrode, measures the voltage drop across the tissue—the cause thereof being described at a later point herein—as a measurement voltage.

The contact 8 is connected to an impedance analyzer unit 9 with a high level of input resistance, which boosts the measurement signal.

The impedance analyzer unit 9 is of a lock-in configuration and breaks down the measurement voltage into a real portion, which is in phase with the measurement current; and an imaginary portion, which is displaced 90° relative to the measurement current phases. To accomplish this the pulse generator 3 is connected at a reference signal input (REF) to the impedance analyzer unit 9. The measurement voltage components obtained are directly proportional to the real portion Re(Z) and the imaginary portion Im(Z) of the impedance (Z=U/I) at a constant measurement current. Re(Z) and Im(Z) form the output signals of the impedance analyzer unit 9. The output signals are input to the control unit 4 by way of a multiplexer with an analog/digital converter 10. From the real portion Re(Z) and the imaginary portion Im(Z) of the impedance Z the control unit 4 calculates the value of the impedance Z and the phase angle, in accordance with the following formula:

$$|Z|=\mathrm{sqr}(Re^2(Z)+Im^2(Z))$$

$$\mathrm{phi}=\arctan Im(Z)/Re(Z)$$

The measurement values, which are re-processed according to the above description embody the myocardial impedance pattern, which is further processed by the control unit 4 as an activity parameter (A). The slow variations of the myocardial impedance pattern are analyzed by the control unit 4 by means of differentiation. In this way the cardiac pacemaker is adapted to slowly varying boundary conditions such as, for example, lifestyle habits, age or medication. In order to improve the pacemaker performance in the event of a short-term physical loading, there is also a motion sensor 11 whose output value is also processed as an activity parameter (A) by the control unit 4. Connected to the output side of the control unit 4, for stimulation of the heart 1, is the pulse generator 3, which generates stimulation pulses, controlled by the heart rate (HR) as ascertained by the control unit. In this respect the cardiac pacemaker operates on the basis of the demand principle, i.e., the cardiac pacemaker stimulates the heart 1 only when, within a given waiting time after a preceding systole of the heart 1, no further systole of the heart 1 due to natural stimulation is detected by the sensor means 5.

The occurrence of a stimulation success immediately after a stimulation pulse output can be detected by an analysis of the myocardial impedance pattern by the control unit 4 after a stimulation pulse output by the stimulation electrode 2. In this way a stimulation failure occurs after a stimulation pulse output, by virtue of a sub-threshold stimulation effect (which can be due to a short-term rise in the stimulation stimulus threshold as a result of altered activity parameters A of the person wearing the cardiac pacemaker), the control unit 4 is capable of initiating a safety stimulation pulse. Such a safety stimulation pulse is generated by the downstream-connected pulse generator 3 and is outputted by the stimulation electrode 2. The safety stimulation pulse can thus be outputted, as required, within a very short time so that the natural cardiac cycle is not disturbed thereby.

Figure 2:
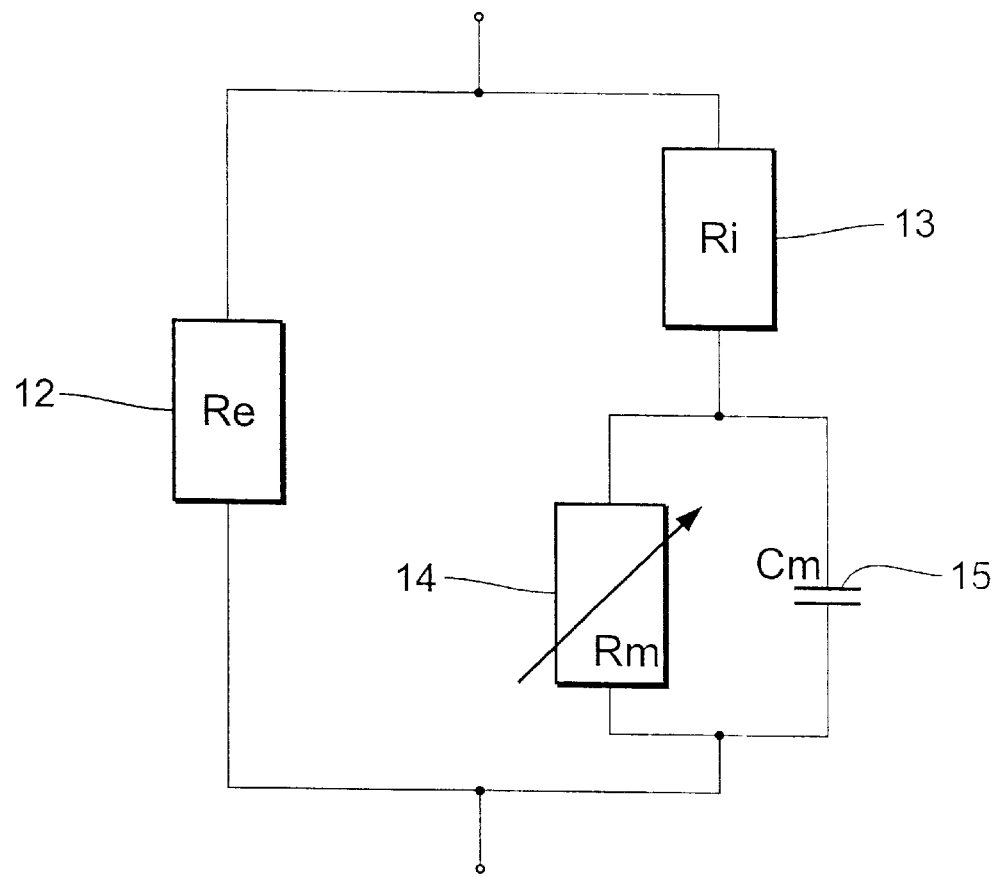
FIG. 2 shows an equivalent circuit diagram for the cardiac muscle tissue for measurement of myocardial impedance.

Short-term detectability of stimulation success is based on an effect of the impedance pattern in the myocardium 6, which can be described with respect to FIG. 2. The equivalent circuit diagram shown herein, in the form of a linear network, represents with resistance (Re) 12 the impedance of the extra-cellular fluid. The resistance (Ri) 13 which is connected in parallel therewith and describes the impedance of the intra-cellular structures and fluid. The downstream-disposed resistance (Rm) 14 stands for the ohmic component of the membrane impedance of the myocardium cell. Finally, the capacitor (Cm) 15 connected in parallel therewith stands for the membrane capacitance of the myocardium cell.

At low frequencies of up to 10 kHz, the tissue impedance is determined by Re. The membrane resistance Rm is very high. Likewise, the reactance of Cm is very great in relation to Re. The current therefore essentially flows by way of Re, the impedance is practically real and reproduces the resistance of the extra-cellular conduction paths which are essentially determined by the specific conductivity of the electrolytic fluid.

In contrast, at high frequencies of over 1 MHz, Ri is the determining factor as the membrane resistance Rm is bridged by the membrane capacitance Cm. In this case, Ri is about 0.3 times Re. The greatest changes in the impedance spectrum are predominantly caused by changes in the membrane properties and ion shifts between the extra-cellular space and the interior of the cells.

The electrical impedance thus affords information about physiological events in the tissue. A systole of the heart 1 after a stimulation pulse is outputted is announced by a brief opening of the $Na^+$-channels for between about 1 and 2 milliseconds and a severe drop in impedance, which that ion shift entails. The stimulation success can be detected immediately after stimulation pulse output by way of the fall in impedance.

Figure 3:
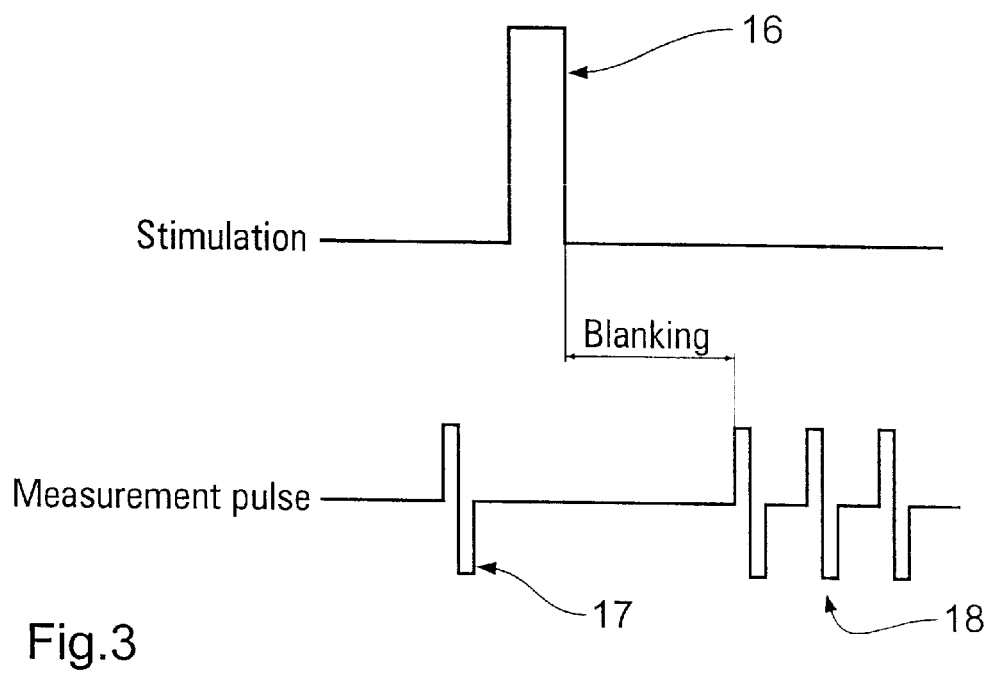
FIG. 3 shows a diagram of the variation in time of a pulse sequence outputted by the cardiac pacemaker during a measurement cycle.

As shown in FIG. 3, detection of a stimulation pulse 16 takes place immediately after expiry of the blanking time by measurement pulses 18. Accordingly, this is at a time in which the heart 1 is still in its diastolic phase, and mechanical work has therefore not yet taken place. Mechanical work (systole) begins only after between about 50 and 70 milliseconds. As stimulation success produces a brief dip in the impedance pattern, stimulation success can be detected by means of the measurement pulses 18. For comparison purposes, the impedance is also ascertained immediately prior to the output of the stimulation pulse 16, by means of a measurement pulse 17.

As a consequence detection of a stimulation failure is rapid and it is preferably possible to output a safety stimulation pulse in a short time and thus physiologically harmless. Furthermore, the detected impedance drop also includes information as to how much the current stimulation amplitude is above the stimulation stimulus threshold. The control unit 4 can use that information for automatic threshold adaptation of the stimulation pulses. Finally, continuous detection of the myocardial impedance pattern is also suitable for the recognition of natural systoles of the heart 1, as there is also a brief drop in impedance during such natural systoles. One procedure according to the invention involves taking suitable consideration of this in the stimulation pulse output by the control unit 4.

In order to minimize the blanking time—in a departure from the embodiment showing the working principle involved—the use of a single fractal electrode for stimulation pulse output and impedance measurement is recommended.

The invention is not limited in terms of its implementation to the preferred embodiment set forth hereinbefore. On the contrary, it is possible to envisage a number of variants which make use of the illustrated structure even in configurations of a basically different kind. In particular, the invention is not limited with respect to activity parameters (A) to the biological parameters listed herein. On the contrary, all biological parameters which exhibit a dependency on the physical or psychological loading of the person wearing the pacemaker can be considered. The same also applies with regard to the electrode arrangement, set forth by way of example, for stimulation and sensor purposes.

What is claimed is:

1. A cardiac pacemaker comprising:
   a pulse generator for generating a stimulation pulse and a measurement pulse;
   at least one stimulation electrode arranged in the region of the heart in signal communication with the pulse generator and designed to output stimulation pulses to the heart;
   at least one sensor means arranged at the myocardium and adapted to detect a myocardial impedance pattern immediately after the cessation of a stimulation pulse and still within the diastolic phase of the heart in response to the measurement pulse; and
   a control unit having at least one output connected to the pulse generator for controlling the stimulation pulse output of the pulse generator, at least one input connected to the at least one sensor means for detecting a successful stimulation of the heart by monitoring the myocardial impedance pattern, the control unit being adapted to control stimulation pulse output of the pulse generator based on the variations in impedance in the myocardial impedance pattern.

2. A cardiac pacemaker as set forth in claim 1, wherein the sensor means is adapted to detect short term dips in impedance.

3. A cardiac pacemaker as set forth in claim 1, wherein the control unit is adapted to trigger a safety stimulation pulse, if a short term dip of impedance is not detected within a predetermined period after the output of a stimulation pulse.

4. A cardiac pacemaker as set forth in claim 1, wherein the stimulation electrode is integrated into the sensor means.

5. A cardiac pacemaker as set forth in claim 4, wherein the stimulation electrode is a fractal electrode.

6. A cardiac pacemaker as set forth in claim 1, wherein for measurement of myocardial impedance pattern on the basis of a current-voltage method the sensor means includes:
   at least one electrode set comprising two contacts arranged in a spaced relationship on the myocardium wherein one contact is supplied with measurement pulses by the pulse generator and the other contact serves as a measurement electrode for ascertaining the myocardial impedance and provides a signal to the control unit.

7. A cardiac pacemaker as set forth in claim 6, wherein one of the two contacts of the sensor means is replaced by the stimulation electrode.

8. A cardiac pacemaker as set forth in claim 6, wherein at least one of the two contacts is of a fractal geometry.

9. A cardiac pacemaker as set forth in claim 6, wherein the measurement pulses are outputted by the pulse generator at a contact at a sampling rate of greater than or equal to 500 Hz.

10. A cardiac pacemaker as set forth in claim 9, wherein the measurement pulses are fed to the myocardial contact only during a predetermined time window.

11. A cardiac pacemaker as set forth in claim 1, wherein measurement of the myocardial impedance pattern is taken between 2 and 10 milliseconds after the stimulation pulse output.

12. A cardiac pacemaker as set forth in claim 1, wherein to ascertain a variation in impedance in the myocardial impedance pattern a measurement of myocardial impedance is taken immediately prior to the output of the stimulation pulse.

13. A cardiac pacemaker as set forth in claim 1, wherein to detect the extent by which a specified stimulation stimulus threshold is exceeded, the control unit ascertains the time delay between the stimulation pulse and a successful stimulation of the heart.

14. A cardiac pacemaker as set forth in claim 1, wherein in the event of a successful stimulation of the heart failing to occur as a result of a sub-threshold stimulation, the control unit actuates the pulse generator for the output of a safety stimulation pulse.

15. A cardiac pacemaker as set forth in claim 1, wherein besides checking the successful stimulation of the heart the control unit also checks natural heart actions.

16. A cardiac pacemaker as set forth in claim 15, wherein for the detection of natural heart actions, the control unit continuously monitors the myocardial impedance pattern and ascertains a natural heart action on the basis of a temporary fall in impedance in the myocardial impedance pattern without a preceeding stimulation pulse output.

17. A cardiac pacemaker as set forth in claim 1, wherein there is provided a motion sensor for the detection of a physical load whose output in the rest condition of the person wearing the cardiac pacemaker assumes a first state and during movement of the person wearing the cardiac pacemaker assumes a second state, wherein the motion sensor is connected on an input of the control unit for influencing stimulation pulse output.

18. A cardiac pacemaker for a patient's heart, comprising:
   at least one stimulation electrode disposed in the right ventricle of the heart;
   a pulse generator, wherein the pulse generator outputs stimulation pulses to the heart via the stimulation electrode and a measurement pulse;
   a control unit connected to the pulse generator for controlling the stimulation pulses output by the pulse generator;
   a sensor electrically connected to the control unit, wherein the sensor checks for stimulation success of the heart by taking a measurement of the heart's myocardial impedance pattern in response to the measurement pulse;
   the sensor being disposed on the myocardium of the heart;
   the sensor being adapted to detect the myocardial impedance pattern immediately after the cessation of the stimulation pulse output during the diastolic phase of the heart;
   the sensor providing a signal to the control unit, wherein the signal is responsive to the detected myocardial impedance pattern;
   the control unit being adapted to control the stimulation pulse output of the pulse generator in response to variations in impedance in the myocardial impedance pattern, as indicated by the sensor.

19. The cardiac pacemaker of claim 18, wherein the sensor is adapted to detect short term impedance dips.

20. The cardiac pacemaker of claim 18, wherein the control unit is adapted to trigger a safety stimulation pulse when a short term impedance dip is not detected by the sensor within a predetermined period after the delivery of a stimulation pulse.

21. The cardiac pacemaker of claim 18, wherein the sensor is integrated within the stimulation electrode.

22. The cardiac pacemaker of claim 18, wherein the stimulation electrode is a fractal electrode.

23. The cardiac pacemaker of claim 18, wherein the sensor comprises at least one electrode set comprising two contacts arranged in a spaced relationship on the myocardium, wherein one contact is supplied with measurement pulses by the pulse generator and the other contact serves as a measurement electrode for ascertaining the myocardial impedance.

24. The cardiac pacemaker of claim 23, wherein the sensor utilizes the stimulation electrode, in place of one of the contacts, for providing measurement pulses to the myocardium.

25. The cardiac pacemaker of claim 23, wherein at least one of the two contacts is of a fractal geometry.

26. The cardiac pacemaker of claim 23, wherein the pulse generator outputs measurement pulses at a sampling rate of at least 500 Hz.

27. The cardiac pacemaker as set forth in claim 23, wherein the measurement pulses are output only during a predetermined time window.

28. The cardiac pacemaker as set forth in claim 18, wherein measurement of the myocardial impedance pattern occurs between 2 and 10 milliseconds after stimulation pulse output.

29. The cardiac pacemaker as set forth in claim 18, wherein to ascertain a variation in impedance in the myocardial impedance pattern a measurement of myocardial impedance is effected immediately prior to stimulation pulse output.

30. The cardiac pacemaker of claim 18, wherein the control unit is adapted to detect the extent by which a stimulus threshold is exceeded by measuring the time interval between a supra-threshold stimulation pulse and a preceding sub-threshold stimulation pulse.

31. The cardiac pacemaker of claim 18, wherein the control unit actuates the pulse generator to output a safety stimulation pulse, if heart stimulation success fails to occur as a result of a subthreshold stimulation.

32. The cardiac pacemaker of claim 18, wherein the control unit implements a check of natural heart action.

33. The cardiac pacemaker of claim 32, wherein the control unit continuously monitors the myocardial impedance pattern and ascertains a natural heart action on the basis of a temporary fall in myocardial impedance without previous stimulation pulse output.

34. The cardiac pacemaker of claim 18, further comprising:
   a motion sensor for the detection of physical loads, the motion sensor being electrically connected to the control unit;
   the motion sensor generating an output signal, the signal having first and second states, the first state corresponding to a rest condition of the person wearing the cardiac pacemaker, the second state corresponding to movement of the person wearing the cardiac pacemaker;
   the control unit being adapted to modify the stimulation pulse in response to the motion sensor's output signal.

* * * * *